(12) United States Patent
Lee et al.

(10) Patent No.: US 10,099,046 B2
(45) Date of Patent: Oct. 16, 2018

(54) SKULL IMPLANT TYPE MEDICATION INJECTION PORT

(71) Applicant: NATIONAL CANCER CENTER, Goyang-si, Gyeonggi-do (KR)

(72) Inventors: Seung Hoon Lee, Seoul (KR); Ho-Shin Gwak, Seoul (KR); Kwang Gi Kim, Seoul (KR); Sang-Hoon Shin, Goyang-si (KR); Heon Yoo, Seoul (KR); Jin Soo Lee, Goyang-si (KR)

(73) Assignee: NATIONAL CANCER CENTER, Goyang-si, Gyeonggi-do (KR)

( * ) Notice: Subject to any disclaimer, the term of this patent is extended or adjusted under 35 U.S.C. 154(b) by 87 days.

(21) Appl. No.: 15/027,018

(22) PCT Filed: Sep. 30, 2014

(86) PCT No.: PCT/KR2014/009177
§ 371 (c)(1),
(2) Date: Apr. 4, 2016

(87) PCT Pub. No.: WO2015/053504
PCT Pub. Date: Apr. 16, 2015

(65) Prior Publication Data
US 2016/0235960 A1    Aug. 18, 2016

(30) Foreign Application Priority Data
Oct. 8, 2013  (KR) .................. 10-2013-0119724

(51) Int. Cl.
*A61M 31/00*  (2006.01)
*A61M 39/02*  (2006.01)

(52) U.S. Cl.
CPC ..... *A61M 39/0247* (2013.01); *A61M 39/0208* (2013.01); *A61M 2039/025* (2013.01);
(Continued)

(58) Field of Classification Search
CPC .. A61M 2039/0205; A61M 2039/0223; A61M 2039/025; A61M 2039/0276;
(Continued)

(56) References Cited

U.S. PATENT DOCUMENTS 4,673,394 A * 6/1987 Fenton, Jr. ........ A61M 5/14276
                                                       128/912
5,222,982 A    6/1993 Ommaya
(Continued)

FOREIGN PATENT DOCUMENTS

JP      2013-150812 A    8/2013
KR   10-2011-0000795 A    1/2011
WO      WO-96-33766 A1   10/1996

OTHER PUBLICATIONS

International Search Report for PCT/KR2014/009177, ISA/KR, Daejeon, dated Oct. 23, 2014 Korean and English).
(Continued)

*Primary Examiner* — Rebecca E Eisenberg
(74) *Attorney, Agent, or Firm* — Harness, Dickey & Pierce, P.L.C.

(57) ABSTRACT

A skull implant medication injection port comprises: a mounted portion placed on an upper section of a port insertion hole in a patient's cranium and a medication inlet on a top surface; a medication injection diaphragm that seals the medication inlet of the mounted portion where a needle for injecting a medication is inserted; a medication storage portion coupled with a bottom of the mounted portion stores the medication injected through the medication injection diaphragm; a medication discharge pipe connected to the medication storage portion discharges the medication stored in the medication storage portion; and a rib formed on a perimeter between the mounted portion and the medication storage portion that has a diameter larger than an inner diameter of the port insertion hole. A height of the mounted
(Continued)

portion is generally about 4 to 7 mm, and a height of the medication storage portion is generally about 2 to 4.2 mm.

10 Claims, 9 Drawing Sheets

(52) U.S. Cl.
CPC ............... *A61M 2039/0205* (2013.01); *A61M 2039/0223* (2013.01); *A61M 2039/0276* (2013.01); *A61M 2039/0282* (2013.01)

(58) Field of Classification Search
CPC ...... A61M 2039/0282; A61M 39/0208; A61M 39/0247
See application file for complete search history.

(56) References Cited

U.S. PATENT DOCUMENTS

| 5,906,596 | A | * | 5/1999 | Tallarida | ........... | A61M 39/0247 |
| | | | | | | 604/175 |
| 5,954,687 | A | | 9/1999 | Baudino | | |
| 2005/0027234 | A1 | * | 2/2005 | Waggoner | .......... | A61B 10/0045 |
| | | | | | | 604/8 |
| 2005/0137537 | A1 | | 6/2005 | Watson et al. | | |
| 2005/0267591 | A1 | * | 12/2005 | Ricci | ................. | A61M 39/0247 |
| | | | | | | 623/23.44 |
| 2009/0198218 | A1 | | 8/2009 | Gill et al. | | |
| 2010/0217236 | A1 | | 8/2010 | Gill et al. | | |
| 2012/0123391 | A1 | | 5/2012 | Gill et al. | | |

OTHER PUBLICATIONS

Written Opinion of the ISA for PCT/KR2014/009177, ISA/KR, Daejeon, dated Oct. 23, 2014 (Korean).

* cited by examiner

[Fig. 1]
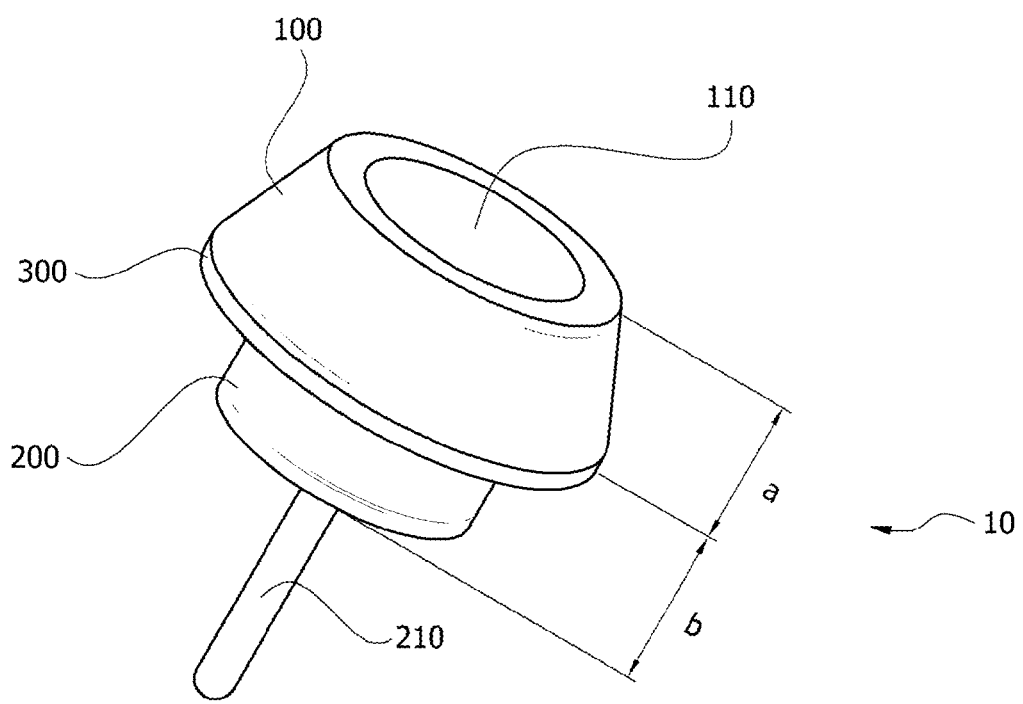
[Fig. 2]
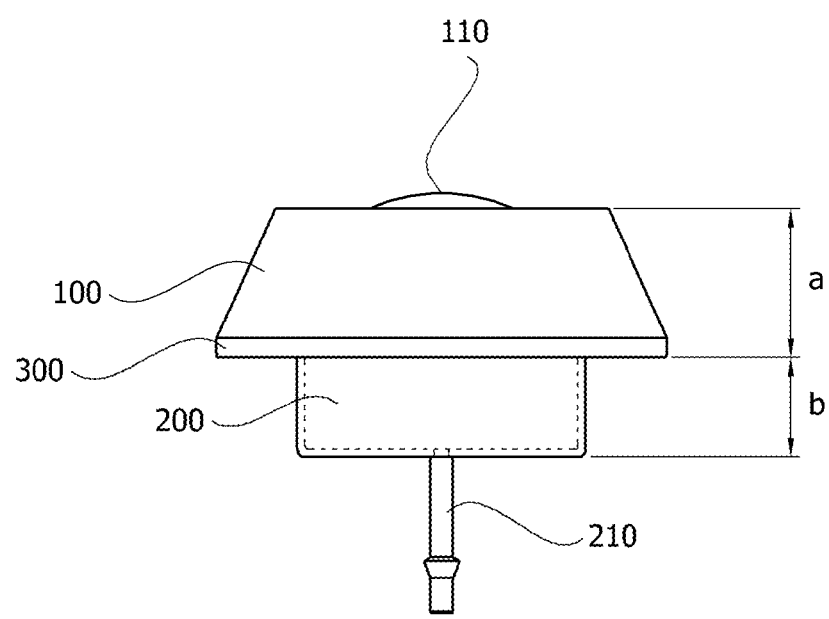

[Fig. 3]
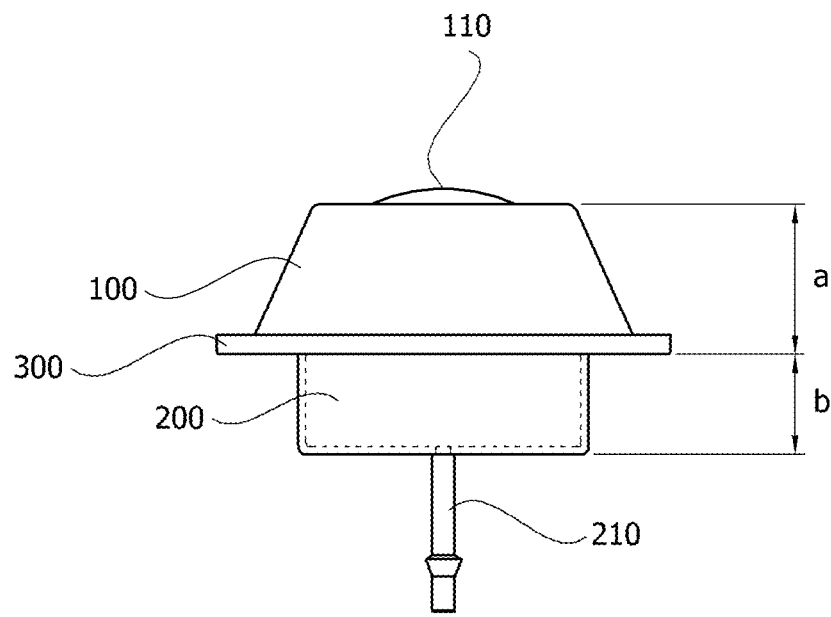
[Fig. 4]
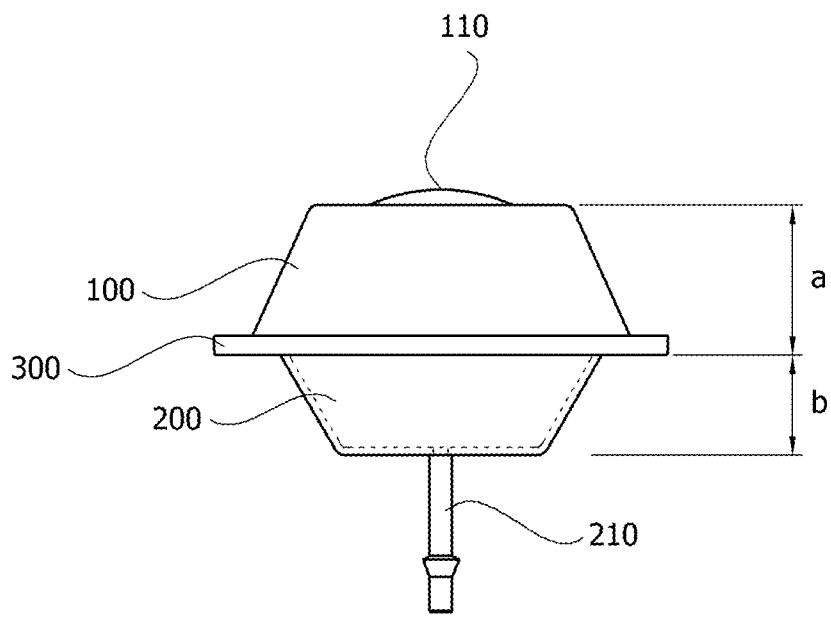

[Fig. 5]
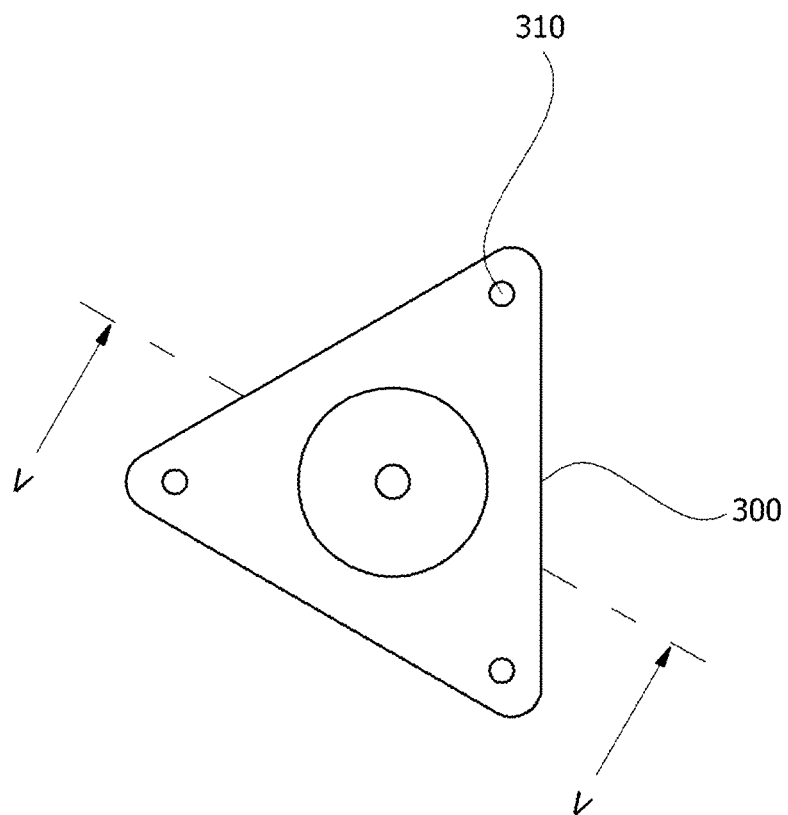

[Fig. 6]
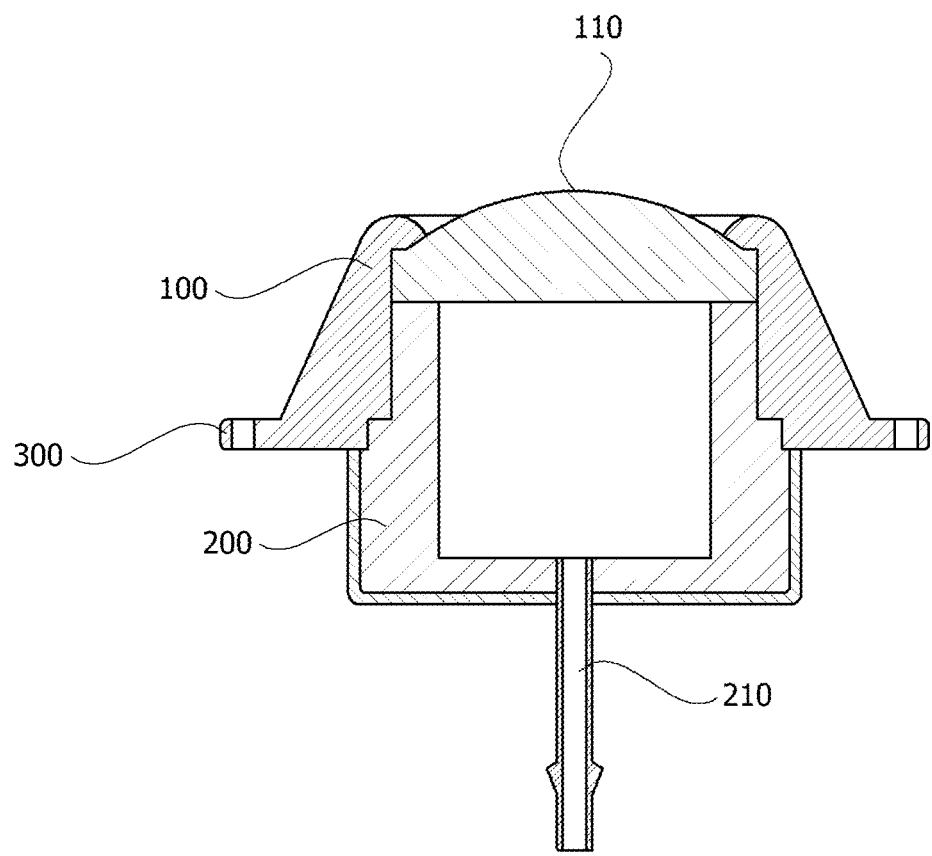

[Fig. 7]
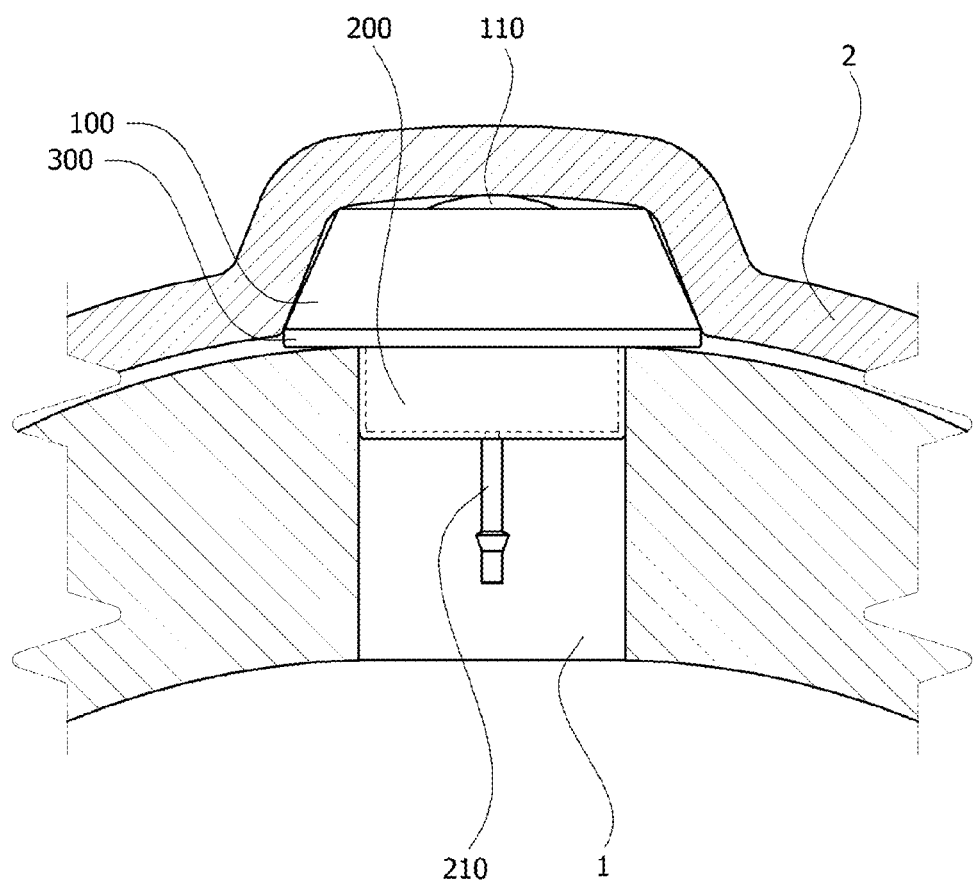

[Fig. 8]
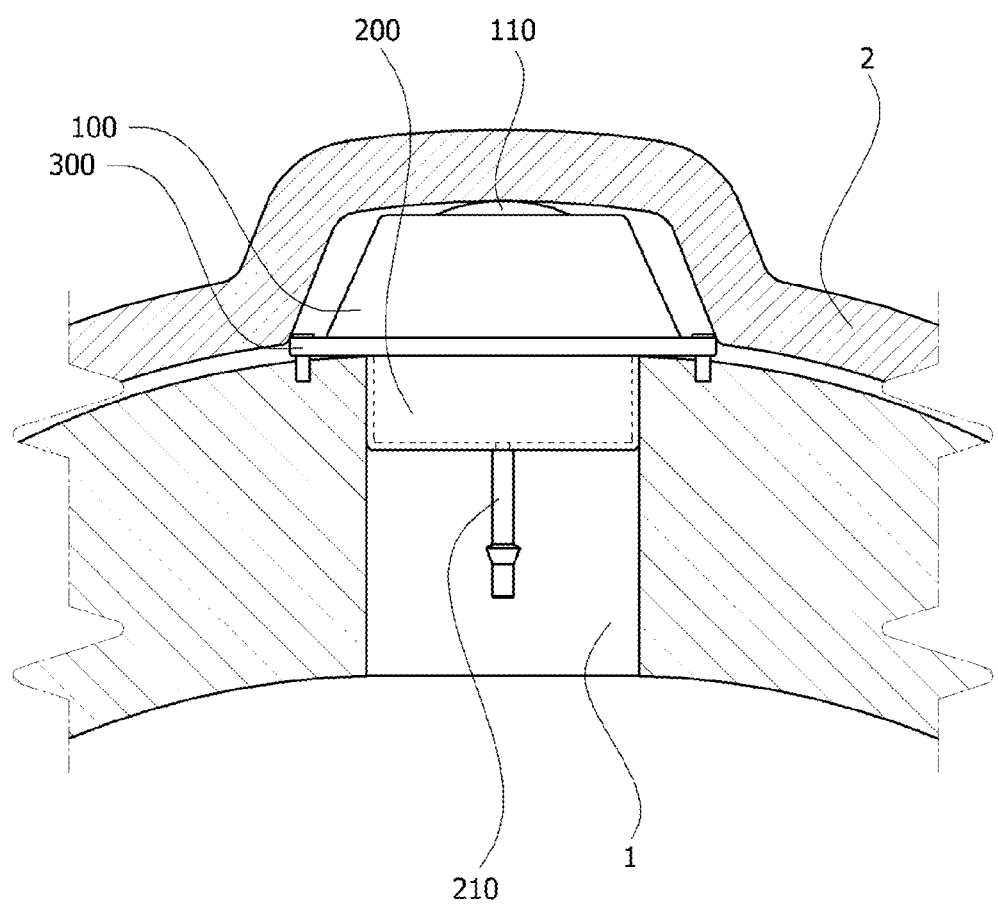

[Fig. 10]
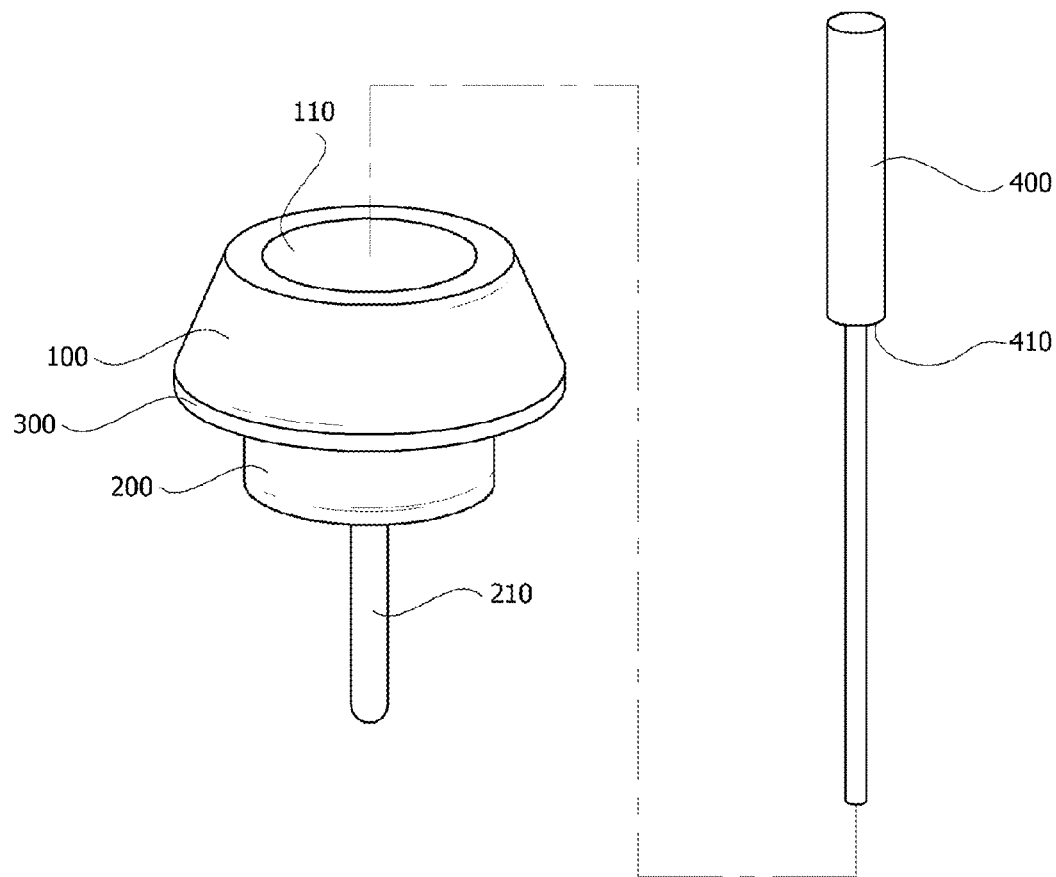

[Fig. 11]
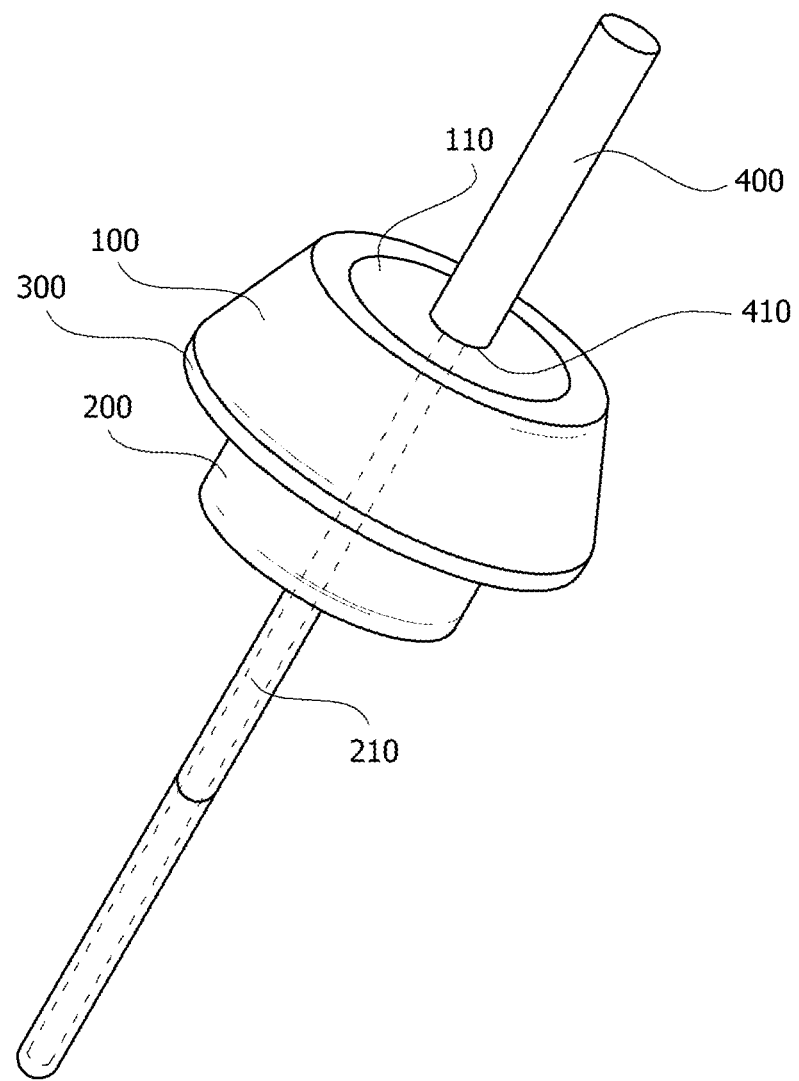

SKULL IMPLANT TYPE MEDICATION INJECTION PORT

CROSS-REFERENCE TO RELATED APPLCATIONS

This application is a 371 U.S. National Stage of International Application No. PCT/KR2014/009177, filed Sep. 30, 2014, which claims the benefit of and priority to Korean Patent Application No. 10-2013-0119724, filed Oct. 8, 2013. The entire disclosures of both of the above applications are incorporated herein by reference.

TECHNICAL FIELD

The present invention relates to a skull implant type medication injection port capable of discharging a medication injected from the outside of a human body into a human body through a medication discharge pipe.

BACKGROUND ART

Generally, a body-implanted medication injection port is a device developed for a patient who suffers from an illness which requires constant performance of continuous or intermittent medication injections over a long period, and a body-implanted medication injection port is capable of discharging a medication injected from the outside to a desired part through a medication discharge pipe while remaining implanted in patient's body.

A cancer patient is a patient who requires constantly performance of continuous or intermittent medication injections. In addition to a periodic injection of anticancer medication for treatment, 50% of all cancer patients require additional injections of painkillers for reducing pain.

Body-implanted medication injection ports may be applied to cancer patients described above and other patients who suffer from severe illnesses which require constant medication injections. Also, body-implanted medication injection ports are not directly exposed to the outside of the body and thus are unlikely to be contaminated or polluted, and have the advantage of allowing patents to go about their daily lives without any inconvenience.

The body-implanted medication injection ports described above are directly connected to arteries or veins and directly transfer medication injected from the outside to the inside of blood vessels generally through medication discharge pipes, but body-implanted medication injection ports are also used for anticancer medication treatment of cancer patients, and more particularly, treatment of brain tumor patients.

However, since conventional body-implanted medication injection ports do not have structures suitable for being inserted into a patient's cranium during a procedure for anticancer medication treatment for a brain tumor patient, the procedure is complicated and an implanted portion remains externally protruded after the procedure.

Also, U.S. Pat. No. 5,222,982 discloses a technology for injecting medication into brain tissue or a cerebral ventricle. However, since a storage portion in the technology is formed of a plastic material, the strength thereof is low and it is difficult to sense it via touch under the scalp. Particularly, when medication is repeatedly injected, the medication frequently leaks under the scalp due to the weak material membrane of an upper hemisphere of the storage portion.

DISCLOSURE

Technical Problem

The present invention provides a skull implant type medication injection port and a skull implant type medication injection system, which improves the degree of convenience of a procedure and an external shape after the procedure.

Technical Solution

One aspect of the present invention provides a skull implant type medication injection port including a mounted portion which is placed on the upper section of a port insertion hole formed in a patient's cranium and comprises a medication inlet formed on a top surface, a medication injection diaphragm configured to seal the medication inlet of the mounted portion into which an injection needle for injecting a medication is inserted, a medication storage portion which is coupled with a bottom of the mounted portion and stores the medication injected through the medication injection diaphragm, a medication discharge pipe connected to the medication storage portion to discharge the medication stored in the medication storage portion, and a rib which is formed on a perimeter between the mounted portion and the medication storage portion and has a diameter greater than an inner diameter of the port insertion hole. Here, a height ratio of the mounted portion to the medication storage portion based on the rib is 1:0.5 to 0.6.

Another aspect of the present invention provides a skull implant type medication injection system including a skull implant type medication injection port and a guide needle which passes through a medication injection diaphragm of the skull implant type medication injection port and is detachably attached to a medication discharge pipe. Here, the guide needle includes a stepped portion formed in an area spaced apart from cutting edge portions by predetermined intervals.

Advantageous Effects

A skull implant type medication injection port in accordance with one embodiment of the present invention includes a mounted portion and a medication storage portion which has a predetermined height ratio based on a rib, thereby making it possible for the skull implant type injection port to be appropriately implanted into a port insertion hole formed in a cranium and be easily identified after implanting the skull implant type injection port.

Also, a skull implant type medication injection system in accordance with one embodiment of the present invention includes a guide needle, thereby simply and precisely being able to perform an implantation of the skull implant type medication injection port.

BRIEF DESCRIPTION OF DRAWINGS

FIG. 1 is a perspective view schematically illustrating a skull implant type medication injection port in accordance with one embodiment of the present invention.

FIG. 2 is a front view of a skull implant type medication injection port in accordance with one embodiment of the present invention.

FIG. 3 is a front view of a skull implant type medication injection port in accordance with one embodiment of the present invention.

FIG. 4 is a front view of a skull implant type medication injection port in accordance with one embodiment of the present invention.

FIG. 5 is a top view of a skull implant type medication injection port in accordance with one embodiment of the present invention.

FIG. 6 is a cross-sectional view of a skull implant type medication injection port in accordance with one embodiment of the present invention.

FIG. 7 is a view illustrating an example of a state in which a medication injection port in accordance with one embodiment of the present invention has been implanted into a patient's cranium.

FIG. 8 is a view illustrating an example of a state in which a medication injection port in accordance with one embodiment of the present invention has been fixed to the cranium using a medical screw.

FIG. 10 is a perspective view of a skull implant type medication injection system in accordance with one embodiment of the present invention.

FIG. 11 is a perspective view of a skull implant type medication injection system in accordance with one embodiment of the present invention.

MODE FOR INVENTION

Figure 9:
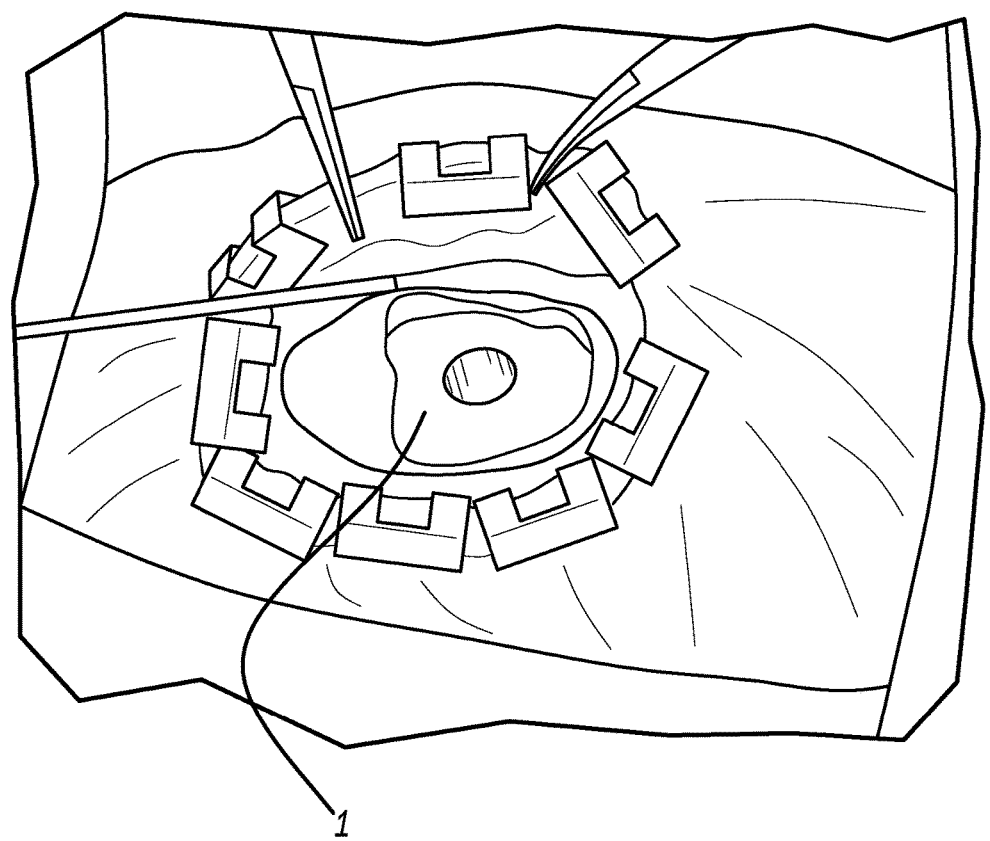
FIG. 9 is a view illustrating an example of a port insertion hole.

The present invention relates to a skull implant type medication injection port including a mounted portion which is placed on the upper section of a port insertion hole formed in a patient's cranium and comprises a medication inlet formed on a top surface, a medication injection diaphragm configured to seal the medication inlet of the mounted portion into which an injection needle for injecting a medication is inserted, a medication storage portion which is coupled with a bottom of the mounted portion and stores the medication injected through the medication injection diaphragm, a medication discharge pipe connected to the medication storage portion to discharge the medication stored in the medication storage portion, and a rib which is formed on a perimeter between the mounted portion and the medication storage portion and has a diameter greater than an inner diameter of the port insertion hole. Here, a height ratio of the mounted portion to the medication storage portion based on the rib is 1:0.5 to 0.6, 1:0.52 to 0.58, or 1:0.55.

Particularly, a height of the mounted portion is 4 to 7 mm and a height of the medication storage portion is 2 to 4 mm. For example, the height of the mounted portion may be 6 mm and the height of the medication storage portion may be 4 mm. Also, a diameter of the mounted portion may be gradually reduced toward a top end surface, and the medication injection diaphragm may be formed of silicone.

In addition, a top end surface and a bottom end surface of the medication storage portion may have substantially identical diameters. As another example, a diameter of the medication storage portion may be gradually reduced from the top end surface toward the bottom end surface. Also, the rib may include at least one fixing hole for fixing the mounted portion to a scalp using a strap or for directly fixing the mounted portion to a cranium using a medical screw.

Further, the present invention also relates to a skull implant type medication injection system including a skull implant type medication injection port and a guide needle which passes through a medication injection diaphragm of the skull implant type medication injection port and is detachably attached to a medication discharge pipe. Here, the guide needle comprises a stepped portion formed in an area spaced apart from pointed end portions by predetermined intervals.

Particularly, a lower cross section of the guide needle based on the stepped portion may have a diameter formed to be smaller than an inner diameter of the medication discharge pipe.

Hereinafter, exemplary embodiments of the present invention will be described in detail with reference to the attached drawings. The terms and words used in the present disclosure and claims should be understood as not being limited to general or lexical meanings. In an aspect that the inventor may properly define the concept of the terms in order to describe the present invention in the best way, the terms should be understood as meanings and concepts appropriate to the technical concept of the present invention.

Accordingly, the embodiments disclosed in the specification and components illustrated in the drawings are merely the most exemplary embodiments, which do not represent the whole technical concept of the present invention. It should be understood that various equivalents and modified examples thereof may exist at the time of filing the present application.

FIG. 1 is a perspective view schematically illustrating a skull implant type medication injection port in accordance with one embodiment of the present invention. FIG. 2 is a front view of a skull implant type medication injection port in accordance with one embodiment of the present invention. FIG. 3 is a front view of a skull implant type medication injection port in accordance with one embodiment of the present invention. FIG. 4 is a front view of a skull implant type medication injection port in accordance with one embodiment of the present invention. FIG. 5 is a top view of a skull implant type medication injection port in accordance with one embodiment of the present invention. FIG. 6 is a cross-sectional view of a skull implant type medication injection port in accordance with one embodiment of the present invention. FIG. 7 is a view illustrating an example of a state in which a medication injection port in accordance with one embodiment of the present invention is implanted into a patient's cranium. FIG. 8 is a view illustrating an example of a state in which a medication injection port in accordance with one embodiment of the present invention is fixed to a cranium using a medical screw. FIG. 9 is a view illustrating an example of a port insertion hole. FIG. 10 is a perspective view of a skull implant type medication injection system in accordance with one embodiment of the present invention. FIG. 11 is a perspective view of a skull implant type medication injection system in accordance with one embodiment of the present invention. Hereinafter, a skull implant type medication injection port in accordance with one embodiment of the present invention will be described with reference to FIGS. 1 to 11.

As shown in FIGS. 1 to 6, a skull implant type medication injection port 10 in accordance with one embodiment of the present invention may include a mounted portion 100, a medication storage portion 200, a medication discharge pipe 210, a rib 300, etc.

Meanwhile, the cranium of humans, unlike a general form of long bones of arms and legs of humans, has a form in which a hard compact bone forms an exterior and a loose cancellous bone is present in the compact bone. The skull implant type medication injection port 10 in accordance with one embodiment of the present invention is mounted in a port insertion hole 1 formed by cutting the compact bone and the cancellous bone into three layers.

First, the mounted portion 100 may be placed on the upper section of the port insertion hole 1 and may include a medication inlet at a top surface thereof. Particularly, to allow the mounted portion 100 to be held by the top of the port insertion hole 1, the rib 300 which has a diameter larger than a diameter of the mounted portion 100 and the inner diameter of the port insertion hole 1 and is horizontally protruded may be included. The rib 300 may include at least one fixing hole 310 to fix the skull implant type medication injection port 10 to a patient's scalp using a strap or to directly fix the skull implant type medication injection port 10 to the cranium using a metal medical screw. Particularly, the rib 300 may have a circular or polygonal shape, and may have any shape capable of being held by the top of the port insertion hole 1.

Also, the mounted portion 100 may be formed of a biocompatible, corrosion-resistant metal, for example, it may be formed of titanium or stainless steel.

A medication injection diaphragm 110 is provided to seal the medication inlet of the mounted portion 100. For example, the medication injection diaphragm 110 may be formed in a disc shape with a diameter larger than that of the medication inlet, may be inserted into a bottom of the mounted portion 100 to allow an edge portion of the medication injection diaphragm 110 to be closely attached to a rim portion of the medication inlet, and may be exposed upward through the medication inlet.

Particularly, the medication injection diaphragm 110 may be formed of an elastic material, such as silicone, to allow an injection needle for injecting a medication to be easily inserted thereinto.

The medication storage portion 200 in accordance with one embodiment of the present invention is coupled with the bottom of the mounted portion 100 and provides a space in which a medication injected through the medication injection diaphragm 110 is stored. The medication storage portion 200 may be formed in a container shape, but may have any shape for containing the medication.

Also, a medication discharge pipe 210 may be coupled with and connected to a bottom end of the medication storage portion 200. The medication discharge pipe 210 refers to a pipe connected to the medication storage portion 200 to discharge the medication stored in the medication storage portion 200. For example, a catheter, which is used in the art to inject medication, may be used.

Meanwhile, a predetermined height ratio of the mounted portion 100 and the medication storage portion 200 is formed in the skull implant type medication injection port 10 in accordance with one embodiment of the present invention.

Particularly, an appropriate total height of the skull implant type medication injection port may be 8 to 12 mm or about 10 mm. In more detail, when the medication injection port in accordance with one embodiment of the present invention is implanted into the port insertion hole 1, the medication injection port is surrounded by a scalp 2 of 4 to 5 mm, and then after implanting, medication is supplied by penetrating a needle with a length of 14 to 16 mm, for example, a Huber needle, into the medication injection port.

A length of the Huber needle inserted into the medication injection port 10, which corresponds to a total length of the skull implant type medication injection port 10 in accordance with one embodiment of the present invention including the scalp 2, may be 8 to 12 mm or about 10 mm.

Also, a height of the mounted portion 100 is 4 to 7 mm, and a height of the medication storage portion 200 is 2 to 4.2 mm. For example, the height of the mounted portion 100 may be 6 mm, and the height of the medication storage portion 200 may be 4 mm.

In more detail, based on the rib 300, a height ratio of the mounted portion 100 to the medication storage portion 200 is 1:0.5 to 0.6, 1:0.52 to 0.58, or 1:0.55, and the height of the medication storage portion 200 may be lower than the height of the mounted portion 100. At this time, to stably dispose the skull implant type medication injection port 10 in accordance with one embodiment of the present invention in the port insertion hole 1, the medication storage portion 200 should be smaller than 4.2 mm, which is an average thickness of the compact bone and the cancellous bone of the cranium.

Also, the height of the medication storage portion 200 may be lower than the height of the mounted portion 100. Particularly, the height of the mounted portion 100 is 4 to 7 mm, and the height of the medication storage portion 200 is 2 to 4.2 mm.

In addition, when the height of the mounted portion 100 is less than 4 mm, it is difficult to identify the medication injection port 10 when injecting a medication into an implanted port. When the height of the mounted portion 100 is more than 7 mm, the medication injection port 10 is easily identified but the scalp 2 may be damaged and the exterior does not look good.

Also, when the height of the medication storage portion 200 is less than 2 mm, there may not be enough space for storing medication and it is difficult to stably mount the medication storage portion 200 in the port insertion hole 1 formed in the scalp 2. Additionally, when the height of the medication storage portion 200 is more than 4.2 mm, the height is greater than a thickness of the compact bone and cancellous bone in an outer portion of a bone which forms the cranium and damages an inside compact bone, and thus it is difficult to stably mount the medication storage portion 200 in the port insertion hole 1.

That is, the height of the mounted portion 100 is formed to be appropriate for identifying a device after implanting the skull implant type injection port to easily inject medication, and the height of the medication storage portion 200 is formed to be appropriate for being implanted into the port insertion hole 1 formed by cutting the cranium. For example, the height of the held portion 100 may be 6 mm, and the height of the medication storage portion 200 may be 4 mm.

Also, an outer diameter of the medication storage portion 200 in accordance with one embodiment of the present invention may be smaller than that of the mounted portion 100. This is to form the port insertion hole 1 with a smaller diameter in a patient's cranium.

Meanwhile, the diameter of the mounted portion 100 may be gradually reduced toward to a top end surface thereof. This is to prevent subcutaneous damage when the skull implant type medication injection port 10 is implanted into the port insertion hole 1.

In addition, the top end surface and bottom end surface of the medication storage portion 200 may have the same diameter. This is to easily fix the medication injection port 10 to the port insertion hole 1 with no additional fixing device. Here, to stably fix the medication injection port to the port insertion hole formed in the cranium, a diameter of the port insertion hole 1 may be substantially identical to an outer diameter of the medication injection port. Also, when the port insertion hole 1 is formed in a patient's cranium, in an aspect of performing a procedure, it is easier to form the diameters of the top and bottom of the port insertion hole 1 to be the same than it is to form them to be different.

As another example, a diameter of the medication storage portion 200 may be gradually reduced toward the bottom end surface. This is to minimize damage of the cranium. Here, the diameter of the medication storage portion 200 may be formed to be smaller than the diameter of the port insertion hole 1.

Also, the medication discharge pipe 210 in accordance with one embodiment of the present invention is connected to the medication storage portion 200 to discharge the medication stored in the medication storage portion 200 into an area inside a patient's body to be treated. For example, a top end of the medication discharge pipe 210 passes through a through hole of the medication storage portion 200 and is then connected below to a medication outlet formed in a center of a bottom surface of the medication storage portion 200.

Also, as shown in FIGS. 7 and 8, the present invention relates to a skull implant type medication injection system 20 which includes the skull implant type medication injection port 10 and a guide needle 400.

Here, the guide needle 400 is provided to more smoothly perform the implantation of the skull implant type medication injection port 10 in accordance with one embodiment of the present invention, may function as a pusher and a stopper, and more particularly, is formed to easily pass through the medication injection diaphragm 110 and to be detachably attached to the medication discharge pipe 210 by being extended lengthwise.

Particularly, the guide needle 400 may include a stepped portion 410 formed at an area spaced apart from cutting edge portions by predetermined intervals. In more detail, lengths of the cutting edge portion and the stepped portion 410 of the guide needle 400 are formed to correspond to the lengths of the medication discharge pipe 210 and the medication injection port. The stepped portion 410 of the guide needle 400 is held by the medication injection diaphragm 110, thereby allowing the guide needle 400 to function as the stopper.

In addition, based on the stepped portion 410, a diameter of a bottom cross section of the guide needle 400 may be smaller than the inner diameter of the medication discharge pipe 210, and a top end of the guide needle 400 may have a larger diameter than that of a bottom end thereof.

The skull implant type medication injection port 10 in accordance with one embodiment of the present invention configured as described above is used while being implanted inside a patient's body, and more particularly, under the skin of a cancer patient who has an illness which requires constant performance of continuous or intermittent medication injections over a long period, for example, a cancer patient who is being treated with anticancer medication. Particularly, the present invention provides the skull implant type medication injection port 10 in accordance with one embodiment of the present invention which improves convenience of a procedure and overcomes a problem of being exposed externally when the skull implant medication injection port 10 is implanted into a patient's cranium for anticancer medication treatment of a brain tumor patient in comparison existing procedures.

FIGS. 9 and 10 are views illustrating examples of a state in which the skull implant type medication injection port 10 in accordance with one embodiment of the present invention has been implanted into a patient's cranium.

As shown in FIG. 11, to insert the skull implant type medication injection port 10 into a cranium of a brain tumor patient, subcutaneous tissue at a position adjacent to a portion of a patient's head to be treated is slightly cut and the port insertion hole 1 is formed in the cranium using a cutting device, etc. Here, a diameter of the port insertion hole is formed to be smaller than a diameter of the rib 300 formed at a perimeter of the mounted portion 100 of the skull implant type medication injection port 10 to allow the rib 300 to be held by the top of the port insertion hole. Accordingly, when the medication injection port 10 is inserted into the port insertion hole 1, the medication injection port 10 may be prevented from completely passing through the port insertion hole 1.

Also, a hole for inserting a medication discharge pipe into the patient's cranium is formed simultaneously along with the forming of the port insertion hole.

Next, the guide needle 400 in accordance with one embodiment of the present invention passes through the medication injection diaphragm 110 and is inserted into the medication discharge pipe 210, and then the stepped portion 410 of the guide needle 400 is held by the medication outlet. After that, the skull implant type medication injection system 20, which includes the skull implant type medication injection port 10 and the guide needle 400, is held by the top of the port insertion hole 1 and is implanted in a desired part by moving the guide needle 400 forward, and then the guide needle 400 is removed.

Next, the mounted portion 100 and the subcutaneous tissue are sewn up using a strap, and the fixing hole 310 formed in the rib 300 of the mounted portion 100 stably fixes the entire skull implant type medication injection port 10, or the mounted portion 100 may be directly fixed to an adjacent part of the cranium using a metal medical screw instead of the strap.

Lastly, the cut part of the subcutaneous tissue is sutured to implant the skull implant type medication injection port 10 into the body, thereby completing the procedure of implanting the medication injection port 10 into the body.

As an example, the mounted portion 100 and the medication storage portion 200 of the skull implant type medication injection port 10 were implanted into the port insertion hole while the heights thereof were changed.

In more detail, the skull implant type medication injection port 10 including the medication storage portion 200 with a height of 6 mm and the mounted portion 100(A) with a height of 7 mm was inserted into the port insertion hole 1. Here, since a height of the medication storage portion 200 is formed higher than a height of the port insertion hole 1, it was not suitable for implantation. Also, when the height of the mounted portion 100 was high, it could be identified easily, but an exterior did not look good.

Next, the skull implant type medication injection port 10 including the medication storage portion 200 with a height of 2 mm and the mounted portion 100 with a height of 3 mm (B) was inserted into the port insertion hole 1. However, since the height of the medication storage portion 200 was too low, there was insufficient space to store an adequate amount of medication, and it was difficult to stably mount the port on insertion hole 1 in the cranium. Also, since the height of the mounted portion 100 was low, it was difficult to identify a device. That is, it could be known that in the case that it is difficult to identify the device after implantation, it is not appropriate for injecting medication into the skull implant type medication injection port 10.

Lastly, the skull implant type medication injection port 10 including the medication storage portion 200 with a height of 4 mm and the mounted portion 100(C) with a height of 5 mm was implanted into the port insertion hole 1. Here it could be seen that the height of the medication storage portion 200 was appropriate for being formed in the cranium and the height of the mounted portion 100 was also easy to identify after implantation (refer to Table 1).

TABLE 1

|  | (A) | (B) | (C) |
|---|---|---|---|
| Height (mm) of Mounted Portion | 7 | 3 | 5 |
| Height (mm) of Medication Storage Portion | 6 | 2 | 4 |
| Implantability | X | X | ○ |

Also, the skull implant type medication injection port 10 in accordance with one embodiment of the present invention may be applied differently depending on a thickness of a human's cranium. An average thickness of a human's cranium is 6.5 mm in the case of males, 7.1 mm in the case of females, and 5 mm in the case of children. Through one experimental example, a height of a compact bone inside a cranium (about 3 mm) was taken into consideration. When the entire height of a medication injection port (8 to 12 mm) was taken into consideration, optimal heights of the mounted portion 100 and the medication storage portion 200 were as provided in Table 2 below.

TABLE 2

|  | Male | Female | Child |
|---|---|---|---|
| Height (mm) of Mounted Portion | 6.5 | 5.9 | 6 |
| Height (mm) of Medication Storage Portion | 3.5 | 4.1 | 2 |

As described above, it should be understood by one of ordinary skill in the art that the present invention can be embodied in other detailed forms without changing the technical concept or essential features thereof. Therefore, all the embodiments described above are examples and should not be understood to be restrictive. The scope of the present invention should be defined by the following claims rather than the above description, and it should be understood that all modifications and modified forms drawn from the concept and the scope of the claims and equivalents thereof are included in the scope of the present invention.

DESCRIPTION OF REFERENCE NUMERALS

1: Port insertion hole 2: Scalp
10: Skull implant type medication injection port 20: Skull implant type medication injection system
100: Mounted portion 110: Medication injection diaphragm
200: Medication storage portion 210: Medication discharge pipe
300: Rib 310: Fixing hole
400: Guide needle 410: Stepped portion

The invention claimed is:

1. A skull implant type medication injection port comprising:
   a mounted portion which is placed on the upper section of a port insertion hole formed in a patient's cranium and comprises a medication inlet formed on a top surface;
   a medication injection diaphragm configured to seal the medication inlet of the mounted portion into which an injection needle for injecting a medication is inserted;
   a medication storage portion which is coupled with a bottom of the mounted portion and stores the medication injected through the medication injection diaphragm;
   a medication discharge pipe connected to the medication storage portion to discharge the medication stored in the medication storage portion; and
   a rib which is formed on a perimeter between the mounted portion and the medication storage portion and has a diameter larger than an inner diameter of the port insertion hole,
   wherein a height ratio of the mounted portion to the medication storage portion based on the rib is 1:0.5 to 0.6, wherein a height of the mounted portion is 4 to 7 mm, and a height of the medication storage portion is 2 to 4.2 mm, wherein an appropriate total height of the skull implant type medication injection port is 8 to 12 mm.

2. The skull implant type medication injection port of claim 1, wherein a diameter of the mounted portion is gradually reduced toward a top end surface.

3. The skull implant type medication injection port of claim 1, wherein the medication injection diaphragm is formed of silicone.

4. The skull implant type medication injection port of claim 1, wherein a top end surface and a bottom end surface of the medication storage portion have substantially identical diameters.

5. The skull implant type medication injection port of claim 1, wherein the rib comprises at least one fixing hole to fix the mounted portion to a scalp using a strap or to directly fix the mounted portion to the cranium using a medical screw.

6. A skull implant type medication injection system comprising:
   the skull implant type medication injection port according to claim 1; and
   a guide needle which passes through a medication injection diaphragm of skull implant type medication injection port and is detachably attached to a medication discharge pipe,
   wherein the guide needle comprises a stepped portion formed in an area spaced apart from cutting edge portions by predetermined intervals.

7. The skull implant type medication injection system of claim 6, wherein the guide needle has a bottom cross section with a diameter formed smaller than an inner diameter of the medication discharge pipe based on the stepped portion.

8. The skull implant type medication injection system of claim 6, wherein a top end of the guide needle has a larger diameter than that of a bottom end.

9. A method of implanting a skull implant type medication injection port, comprising:
   (a) forming a port insertion hole in a patient's cranium;
   (b) allowing a guide needle to pass through a medication injection diaphragm of the medication injection port according to claim 1, and to be inserted into the medication discharge pipe to prepare an implantation of the medication injection port;
   (c) holding the prepared medication injection port by the port insertion hole and moving the guide needle forward; and
   (d) removing the guide needle from the medication injection port and implanting the medication injection port.

10. The method of claim 9, further comprising fixing the implanted medication injection port and then suturing the upper section of the medication injection port.

\* \* \* \* \*